United States Patent [19]

Hermes et al.

[11] Patent Number: 5,051,272
[45] Date of Patent: Sep. 24, 1991

[54] METHOD FOR IMPROVING THE STORAGE STABILITY OF A POLYMERIC ARTICLE SUSCEPTIBLE TO HYDROLYTIC DEGRADATION AND RESULTING ARTICLE

[75] Inventors: Matthew E. Hermes, Easton; Ross R. Muth, Brookfield, both of Conn.

[73] Assignee: United States Surgical Corporation, Norwalk, Conn.

[21] Appl. No.: 221,308

[22] Filed: Jul. 19, 1988

[51] Int. Cl.$^5$ ............................................. A01N 1/02
[52] U.S. Cl. ........................ 427/2; 252/400.61; 252/400.62; 252/407; 428/411.1; 604/304; 606/157; 606/219; 606/231; 623/11; 623/16
[58] Field of Search ............... 128/335.5; 427/2; 606/228–231, 157, 219; 428/411.1; 604/304; 623/11, 16; 528/354; 252/407, 400.61, 400.62

[56] References Cited

U.S. PATENT DOCUMENTS

| | | | |
|---|---|---|---|
| Re. 28,281 | 12/1974 | Bridgeford | 426/105 X |
| 3,413,079 | 11/1968 | Rich, Jr. | 8/130.1 |
| 3,531,561 | 9/1970 | Trehu | 264/210 |
| 3,626,948 | 12/1971 | Glick et al. | 128/335.5 |
| 3,636,956 | 1/1972 | Schneider | 528/354 X |
| 3,665,927 | 5/1972 | Kurtz | 128/335.5 X |
| 3,728,839 | 4/1973 | Glick | 206/63.3 X |
| 3,772,420 | 11/1973 | Glick et al. | 264/202 |
| 3,839,524 | 10/1974 | Adams et al. | 264/231 |
| 4,013,773 | 3/1977 | Murakami et al. | 426/650 X |
| 4,081,493 | 3/1978 | Kazama et al. | 260/859 PV |
| 4,105,034 | 8/1978 | Shalaby et al. | 128/335.5 |
| 4,126,428 | 11/1978 | Rude | 51/295 |
| 4,135,622 | 1/1979 | Glick | 206/63.3 |
| 4,157,085 | 6/1979 | Austad | 128/1 R |
| 4,185,637 | 1/1980 | Mattei | 128/335.5 |
| 4,201,216 | 5/1980 | Mattei | 128/335.5 |
| 4,412,986 | 11/1983 | Kawata et al. | 424/80 |
| 4,523,591 | 6/1985 | Kaplan et al. | 128/335.5 X |
| 4,532,929 | 8/1985 | Mattei et al. | 128/335.5 |
| 4,624,256 | 11/1986 | Messior et al. | 128/335.5 |
| 4,705,820 | 11/1987 | Wang et al. | 427/2 X |
| 4,711,241 | 12/1987 | Lehmann | 427/2 X |

FOREIGN PATENT DOCUMENTS 2092444B 11/1985 United Kingdom.

Primary Examiner—Michael Lusignan
Attorney, Agent, or Firm—Thomas R. Bremer; Peter G. Dilworth; Rocco S. Barrese

[57] ABSTRACT

The storage stability of a polymeric article susceptible to hydrolytic degradation, e.g., an absorbable suture, is improved by applying a storage stabilizing amount of a mixture comprising at least one water soluble hygroscopic polyhydroxy compound and/or ester thereof, e.g., glycerol, monoacetin, diacetin, and the like, and at least one compound having the general formula

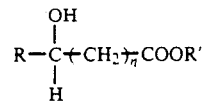

and hydreates thereof to the article as storage stabilizing agent, said agent being retained by the article prior to sealing of the enclosure in which the suture is packaged.

48 Claims, No Drawings

METHOD FOR IMPROVING THE STORAGE STABILITY OF A POLYMERIC ARTICLE SUSCEPTIBLE TO HYDROLYTIC DEGRADATION AND RESULTING ARTICLE

CROSS-REFERENCE TO RELATED APPLICATION

This application is related to copending, commonly assigned, U.S. application Ser. No. 089,735, filed Aug. 26, 1987, now abandoned, the entire contents of which are incorporated herein by reference.

BACKGROUND OF THE INVENTION

This invention provides a method for improving the storage stability of polymeric articles having an inherent tendency to undergo degradation when exposed to water or a humid atmosphere, probably as a result of hydrolysis. More particularly, the invention is directed to improving the storage stability of articles and devices such as absorbable surgical sutures, clips, staples, implants, prostheses and the like, fabricated from polymers which are susceptible to hydrolytic degradation, notably, polymers and copolymers of glycolic acid (i.e., hydroxyacetic acid), the cyclic dimer of glycolic acid ("glycolide"), lactic acid, the cyclic dimer of lactic acid ("lactide") and related monomers.

Polymers and copolymers of the foregoing kind and absorbable surgical devices made therefrom are well known. See, e.g., U.S. Pat. Nos. 2,668,162; 2,703,316; 2,758,987; 3,225,766; 3,297,033; 3,422,181; 3,531,561; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,060,089; 4,137,921; 4,157,437; 4,234,775; 4,237,920; 4,300,565; and 4,523,591; U.K. Patent No. 779,291; D. K. Gilding et al., "Biodegradable polymers for use in surgery—polyglycolic/poly(lactic acid) homo- and co-polymers: 1, *Polymer*, Volume 20, pages 1459-1464 (1979), and D. F. Williams (ed.), *Biocompatibility of Clinical Implant Materials*, Vol. II, ch. 9; "Biodegradable Polymers" (1981). The biodegradability of these polymers/copolymers is believed to be due to the hydrolytic attack of their ester linkages by aqueous body fluids although the exact mechanism involved has been a matter of speculation.

An absorbable suture (or other aqueous body fluid-absorbable article) may experience prolonged storage before use, e.g., periods of several months and sometimes even several years. In order to prevent water or humidity in the storage environment from contacting the suture and compromising its in vivo strength to the point where the suture is no longer serviceable, it is common practice to package the suture in an essentially moisture impermeable enclosure. However as noted in U.S. Pat. Nos. 3,728,839 and 4,135,622, any package material which prevents the entry of moisture will also prevent the escape of moisture. Thus, any moisture associated with or absorbed by the suture at the time it is packaged will tend to remain in the package for the entire period of its storage.

According to aforesaid U.S. Pat. Nos. 3,728,839 and 4,135,622, the in-vivo strength of polyglycolic acid surgical elements such as sutures undergoes significant deterioration on long term standing in the package even on exposure of the contents to very small amounts of water for very short periods of time, e.g., 20 minutes or less, just prior to packaging due to the aforenoted tendency of a moisture impervious package to seal the moisture in with the suture.

To prevent hydrolytic degradation of the suture or to minimize its extent, U.S. Pat. Nos. 3,728,839 and 4,135,622 disclose removing moisture from the suture before sealing the package so that no more than about 0.5 percent of water by weight of suture remains in the package once the package is sealed. This approach to improving the suture's storage stability, while effective, is in practice difficult and expensive to carry out. Prior to sealing the suture within its moisture impervious package, it is essential that the suture be "bone dry", a condition achieved by heating the suture for a sufficient period to remove the water therefrom, e.g., 180°-188° for 1 hour under a 26 inch vacuum. However, once the water is removed, the suture cannot be allowed to contact a moisture-containing environment even for a limited duration since as previously noted, even brief exposure to moisture can cause severe deterioration of suture in vivo strength. It therefore becomes necessary following the water removal step to temporarily store the suture in a dry area, i.e., an environment which is essentially free of moisture, where the possibility of contact with moisture is largely eliminated.

Considered in their entirety, these operations for improving the storage stability of absorbable sutures and other surgical devices which are susceptible to hydrolytic degradation amount to a time consuming, expensive and relatively complex solution to the storage stability problem.

In an attempt to overcome the disadvantages associated with storage stabilizing procedures described in U.S Pat. Nos. 3,728,839 and 4,135,622, U.S. patent application Ser. No. 089,735, filed Aug. 26, 1987, the entire contents of which are incorporated herein by reference, discloses a method for improving the storage stability of a polymeric article susceptible to hydrolysis which comprises applying a storage stabilizing amount of at least one water soluble hygroscopic polyhydroxy compound or ester thereof to the polymeric article as a storage stabilizing agent therefor. Such method requires neither a diminution of the article's pre-packaged moisture content nor temporary storage of the article in an artificially-maintained bone dry environment prior to completion of the packaging operation. A problem associated with the afore-described method of said U.S. application Ser. No. 089,735 has been migration of the hygroscopic polyhydroxy compound or ester thereof from the polymeric article to the surrounding packaging material thereby reducing the otherwise desired storage stabilizing effects of the polyhydroxy compound or ester thereof.

SUMMARY OF THE INVENTION

Accordingly, it is an object of the present invention to overcome the aforenoted disadvantages associated with the storage stabilizing method described in U.S. Pat. Nos. 3,728,839 and 4,135,622 and said copending U.S. application Ser. No. 089,735.

It is another object of this invention to provide a method for improving the storage stability of a polymeric article susceptible to hydrolysis, e.g., an absorbable surgical article such as a suture based in whole or in part on a polyester polymer or copolymer such as polyglycolic acid, lactide-glycolide copolymer, polydioxanone, polytrimethylene carbonate, polyalkylene glycol, polycaprolactone, their copolymers, etc., which requires neither a diminution of the article's pre-packaged moisture content nor temporary storage of the article in an artificially-maintained bone dry environment prior to completion of the packaging operation.

These and other objects are accomplished herein by providing a method for improving the storage stability of a polymeric article susceptible to hydrolysis which comprises applying a storage stabilizing amount of a mixture of at least one water soluble hygroscopic polyhydroxy compound or ester thereof and a compound having the general formula

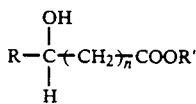

wherein R is hydrogen or methyl, R' is alkali metal or alkaline earth metal, and n is 0 or 1 and hydrates thereof, to the polymeric article, as a storage stabilizing agent therefor.

Ordinarily, the foregoing method can be carried out upon the polymeric article without the need to reduce its moisture level, either before or after applying the stabilizing agent thereto, to a very low level, e.g., to a state of being bone dry as in U.S. Pat. Nos. 3,728,839 and 4,135,622, since entirely acceptable levels of storage stability can be achieved without resorting to such drastic moisture reduction efforts. Similarly, it is altogether unnecessary to maintain the article in a bone dry environment at any time following its manufacture and preceding the completion of its packaging as in the aforesaid patents. Once the article is contacted with the storage stabilizing agent which will thereafter be retained on and/or within the polymeric article, for example, by adhering to its surfaces and/or being sorbed by the polymeric composition of which the article is constructed, the article can be immediately packaged since all that is necessary to effect its long term hydrolytic stability will have been accomplished by the storage stabilizing agent application operation. Such being the case, the storage stabilizing method of the present invention possesses the advantages of simplicity, economy and a level of production efficiency unattainable by the storage stabilizing method described in U.S. Pat. Nos. 3,728,839 and 4,135,622.

In addition to imparting an enhanced degree of storage stability upon polymeric articles which are subject to hydrolytic degradation, practice of the present invention may confer other benefits as well. So, for example, an absorbable suture which has been filled with a storage stabilizing amount of, e.g., a mixture of glycerol and calcium lactate in accordance with the method herein, has been found to exhibit better flexibility and "hand" characteristics than the untreated suture. Moreover, since the hygroscopic compounds useful in the practice of this invention are generally capable of dissolving a number of medico-surgically useful substances, they can be used as vehicles to deliver such substances to a wound or surgical site at the time the suture (or other absorbable surgical device) is introduced into the body.

The term "filled" as used herein refers to the association of the polymeric article with a storage stabilizing amount of storage stabilizing agent whether this association be one in which the storage stabilizing agent is absorbed by the polymeric article, is present on the surfaces thereof or is a combination of the two.

DETAILED DESCRIPTION OF THE INVENTION

A characteristic which the polymeric articles to be contacted with a storage stabilizing agent in accordance with this invention share in common is their relatively high susceptibility to undergoing destructive hydrolysis over a period of storage. Generally, this is an inherent characteristic of polymers and copolymers possessing a significant number of short-chain polyester linkages or other readily hydrolyzable linkages in their structure as, for example, is the case with polyglycolic acid, lactideglycolide polymers, polydioxanone, polyalkylene glycols, polytrimethylene carbonate, polycaprolactone, their copolymers, and related materials. While the invention is particularly useful for application to absorbable sutures both of the monofilament and multifilament type (e.g., those of the braided variety which are especially hygroscopic) fabricated from polymers and copolymers of this kind, it is applicable to other types of surgically useful articles as well, e.g., those disclosed in U.S. Pat. No. 4,135,622, including without limitation, absorbable surgical clips, staples, sponges, gauze, implants and prostheses for reconstructing bone tissue, blood vessels, and so forth.

The useful storage stabilizing agents of the present invention are mixtures comprising at least one water soluble hygroscopic polyhydroxy compound or ester thereof and at least one compound having the general formula

wherein R, R' and n are as described hereinabove. Preferably, the components which make up the stabilizing agent of the present invention have no appreciable toxicity for the body at the levels present. With these requirements in mind, those skilled in the art are readily capable of identifying any number of compounds which may be useful in the practice of this invention. Among the specific water-soluble hygroscopic polyhydroxy compounds or esters thereof which can be used herein with generally good results are glycerol and its mono- and diesters derived from low molecular weight carboxylic acids, e.g., monoacetin and diacetin (respectively, glyceryl monoacetate and glyceryl diacetate), ethylene glycol, diethylene glycol, triethylene glycol, 1,3-propanediol, trimethylolethane, trimethylolpropane, pentaerythritol, sorbitol, and the like. Glycerol is especially preferred. Mixtures of the afore-discussed polyhydroxy compounds or esters, e.g., sorbitol dissolved in glycerol, glycerol combined with monoacetin and/or diacetin, etc., are also useful. Compounds within the general formula

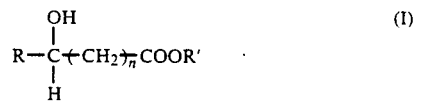

useful in formulating the stabilizing agent mixture of the present invention, include, for example, salts of lactic acid such as calcium lactate, potassium lactate, sodium lactate, salts of glycolic acid, such as calcium glycolate, potassium glycolate, sodium glycolate, salts of 3-hydroxy propanoic acid, such as the calcium, potassium and sodium salts thereof, salts of 3-hydroxybutanoic acid, such as the calcium, potassium and sodium salts thereof and the like. As stated hereinbefore, hydrates of the compounds within the scope of formual I hereinabove are also within the scope of the present invention. Calcium lactate, especially calcium lactate pentahydrate, is particularly preferred.

If necessary or desirable, the stabilizing agent can be dissolved in any suitable non-aqueous solvent or combination of solvents prior to use. To be suitable, the solvent must (1) be miscible with the storage stabilizing agent at the concentration of the latter, (2) have a sufficiently high vapor pressure to be readily removed by evaporation, (3) not appreciably affect the integrity of the polymeric article and (4) capable, in combination with the storage stabilizing agent, of wetting the surface of the surgical article. Applying these criteria to a preferred storage stabilizing agent, glycerol and calcium lactate, lower alcohols such as methanol and ethanol are entirely suitable solvent carriers.

Preparing the storage stabilizing agent of the present invention is a relatively simple procedure. For example, in the case of glycerol and calcium lactate, the desired amount of glycerol is first introduced to a container, followed by the addition thereto of the desired amount of calcium lactate. If no solvent is to be used, the mixture is then thoroughly mixed. In the event a solvent is desired, the solvent such as methanol is added to the mixture of glycerol and calcium lactate and the solution is then thoroughly mixed to dissolve the compounds.

Generally, the stabilizing agent of the present invention is comprised of a mixture of a compound within formula I hereinabove, such as calcium lactate, and a water soluble hygroscopic polyhydroxy compound, such as glycerol, in a weight ratio of between about 1:1 to about 1:10, most preferably 1:7, respectively. When a solvent, such as methanol, is utilized in the preparation of the stabilizing agent, the solvent is employed in amounts to provide a solution concentration of from about 20% to about 50%, preferably about 30% to about 45%, by weight of the compound of formula I hereinabove, such as glycerol, based on the total weight of the solution.

Application of the storage stabilizing agent to the polymeric article can be carried out in any number of ways. Thus, for example, the article can be submerged in the storage stabilizing agent or solution thereof until at least a storage stabilizing amount of the stabilizing agent is acquired or otherwise retained by the article, even after the optional removal of any excess agent and/or accompanying solvent (if present) such as by drainage, wiping, evaporation, etc. In many cases, contact times on the order of from just a few seconds, e.g., about 10 seconds or so, to several hours, e.g., about 2 hours and even longer, are sufficient to impart a substantial improvement in the storage stability of the treated article compared to the same type of article which has not been treated with a storage stabilizing agent.

The foregoing submersion method of contacting the polymeric article with storage stabilizing agent can be conducted continuously or in batch. Thus, in the case of an absorbable suture, a running length of the suture can be continuously passed through a quantity of the stabilizing agent at a velocity which has been previously determined to provide the necessary degree of exposure, or contact time, of the suture with the storage stabilizing agent. As the suture emerges from the storage stabilizing agent, it can be passed through a wiper or similar device to remove excess agent prior to the packaging operation. In a batch operation, a quantity of suture is merely submerged within the storage stabilizing agent for the requisite period of time with any excess agent being removed from the suture if desired.

Alternatively, the storage stabilizing agent and solutions thereof can be applied by spraying, brushing, wiping, etc., on the surfaces of the polymeric articles such that the latter receive and retain at least a storage stabilizing amount of the agent. Yet another procedure which can be used to apply the storage stabilizing agent involves inserting the polymeric article in a package containing an effective amount of the agent such that intimate contact between the polymeric article and the agent will be achieved.

Whatever the contacting procedure employed, it is necessary that the article being treated acquire a storage stabilizing amount of the storage stabilizing agent. In general, amounts of from about 2 to about 25, and preferably from about 5 to about 15 weight percent, of storage stabilizing agent (exclusive of any solvent) by weight of the polymeric article contacted therewith is sufficient to provide significantly improved storage stability compared to that of the untreated article.

The method of the invention can be practiced in conjunction with other known and conventional procedures such as sterilization. Known and conventional packaging techniques and materials are also contemplated. As previously stated, an advantage of the present invention lies in its ability to provide enhanced storage stability in a polymeric article susceptible to hydrolytic degradation without having to eliminate all but a small amount of moisture from the article and maintain the article in an especially dry environment until the final package sealing operation as disclosed in U.S. Pat. Nos. 3,728,839 and 4,135,622. While the present invention can be practiced with a suture or other article which has been treated in this manner, there is no necessity of doing so and for reasons of simplicity, economy and production efficiency, it is preferred that the article to be contacted with storage stabilizing agent in accordance with this invention not receive the treatment described in the aforesaid patents.

It is preferred that the method of this invention be practiced upon a polymeric article whose moisture level has equilibrated to that of the surrounding atmosphere, e.g., from about 5 percent to about 40 percent relative humidity or even higher. Such a moisture content in the atmosphere will typically result in a stabilized surgical article possessing an amount of moisture in the range of from about 0.3 to about 1.5 weight percent or more. Moisture levels within this range, while not tolerated by the packaging method and packaged synthetic surgical element of U.S. Pat. Nos. 3,728,839 and 4,135,622, have no appreciably deleterious effect on the long term in vivo strength of polymeric articles contacted with a storage stabilizing agent in accordance with the present invention. Thus, the polymeric article treated with storage stabilizing agent can, if desired, be packaged at relatively high levels of relative humidity, e.g., those just mentioned.

It can be advantageous to apply one or more coating compositions to the storage stabilized article of this invention where particular functional properties are desired. Thus, for example, in the case of an absorbable suture which has been treated with glycerol for improved long term storage, the storage stabilized article centrifugal force 3,000 Gs. The results are shown in Table I.

TABLE I

| Sample | Uncentrifuged wt % G | Uncentrifuged wt % CaL | Centrifuged wt % G | Centrifuged wt % CaL | % Retention G | % Retention CaL |
|---|---|---|---|---|---|---|
| A: Size 3/0 Synthetic Absorbable Suture | 21.7 | — | 10.5 ± 3 | — | 48 ± 14 | — |
| B: Size 1/0 Synthetic Absorbable Suture | 3.4 | 2.7 | 3.3 | 2.8 | about 100 | about 100 |
| C: Size 3/0 Synthetic Absorbable Suture | 14.9 | 2.2 | 12.9 | 1.7 | 87 | 78 |
| D: Size 3/0 Synthetic Absorbable Suture | 15.4 | 3.8 | 9.9 | 2.7 | 64 | 71 |

G = glycerol
CaL = calcium lactate.5 $H_2O$
absorbable sutures = fibers from glycolide/lactide copolymers can be coated with a polyethylene oxide-polypropylene oxide block copolymer or polyalkylene glycol, either of which has been further polymerized with glycolide monomer and lactide monomer or glycolide/lactide copolymer to improve surface lubricity and facilitate knot tie-down as disclosed in commonly assigned U.S. patent application Ser. Nos. 089,733 filed Aug. 26, 1987 and 089,734 filed Aug. 26, 1987, the entire contents of which are incorporated herein by reference.

As previously noted, it can be advantageous to employ the storage stabilizing agent as a carrier for one or more medico-surgically useful substances, e.g., those which accelerate or otherwise beneficially modify the healing process when applied to a wound or surgical site. In general, any biologically active material which is soluble in and otherwise compatible with the selected storage stabilizing agent can be incorporated therein in therapeutically useful amounts. So, for example, a suture can be filled with storage stabilizing agent containing a therapeutic agent which will be deposited at the sutured site. The therapeutic agent may be chosen for its antimicrobial properties, capability for promoting wound repair and/or tissue growth or for specific indications such as thrombolysis. Antimicrobial agents such as broad spectrum antibiotics (gentamycin sulphate, erythromycin or derivatized glycopeptides) which are slowly released into the tissue can be applied in this manner to aid in combating clinical and sub-clinical infections in a surgical or trauma wound site. To promote wound repair and/or tissue growth, one or several growth promoting factors can be added to the storage stabilizing agent, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dismutase to scavenge tissue damaging free radicals, tumor necrosis factor for cancer therapy or colony stimulating factor and interferon, interleukin-2 or other lymphokine to enhance the immune system.

The following examples are illustrative of the storage stabilizing method and storage stabilized polymeric article of this invention.

EXAMPLE 1

Glycerol filled and glycerol/calcium lactate filled braided sutures were centrifuged using a Clay Adams bench top lab centrifuge in order to compare retention as a percentage of baseline fill. Four samples were spun after collecting baseline data on the uncentrifuged sample. The centrifuge was run for 15 minutes at top speed, The foregoing data indicate that adding calcium lactate to glycerol gives an increase in glycerol retention.

EXAMPLE 2

Samples of calcium lactate/glycerin-filled braided sutures show equally improved stability to storage compared to glycerin filled braid without calcium lactate s shown in Table II (Compare C and D to A and E). In both cases, the stability is excellent compared to braid without glycerin and equilibrated at about the same moisture level.

TABLE II

| Sample | C | D | A | E | F |
|---|---|---|---|---|---|
| % Glycerin | 14.9 | 15.4 | 21.7 | 10 | 0 |
| % Ca lactate | 2.2 | 3.8 | 0 | 0 | 0 |
| % Water | 0.55 | 0.55 | 0.45 | 0.45 | 0.45 |
| Storage Time in weeks at 56° C. | % Strength Retained After 2 Weeks In Vitro at 37° C. And After Accelerated Storage at 56° C. | | | | |
| 0 | 50 | 50 | 50 | 50 | 50 |
| 1 | 64 | 55 | 53 | 54 | 35 |
| 2 | 53 | 56 | 50 | 39 | 13 |
| 3 | 49 | 50 | 45 | 32 | 22 |
| 4 | 65 | 56 | 39 | 36 | 15 |
| 5 |  |  | 36 | 43 |  |
| 6 |  |  |  | 36 | 11 |

Obviously, other modifications and variations of the present invention are possible in the light of the above teachings. It is, therefore, to be understood that changes may be made in the particular embodiments of this invention which are within the full intended scope of the invention as defined by the appended claims.

What is claimed is:

1. A method for improving the storage stability of a polymeric article susceptible to hydrolysis which comprises applying a storage stabilizing amount of a mixture comprising effective amounts of at least one water soluble hygroscopic polyhydroxy compound or ester thereof and at least one compound having the general formula

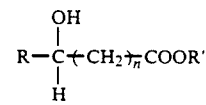

wherein R is hydrogen or methyl, R' is a metal selected from the group consisting of alkali metal and alkaline earth metal and n is 0 or 1 and hydrates thereof, to the polymeric article, as storage stabilizing agent therefor.

2. The method of claim 1 wherein the polymeric article is fabricated in whole or in part from a polymer or copolymer possessing short-chain polyester linkages or other readily hydrolyzable linkages.

3. The method of claim 1 wherein the polymeric article is fabricated in whole or in part from a polymer or copolymer of glycolic acid, glycolide, lactic acid, lactide dioxanone, trimethylene carbonate, caprolactone, polyalkylene glycol or combination thereof.

4. The method of claim 1 wherein the polymeric article is an absorbable suture fabricated in whole or in part from a polymer or copolymer of glycolic acid, glycolide, lactic acid, lactide, dioxanone, trimethylene carbonate, caprolactone, polyalkylene glycol, or combination thereof.

5. The method of claim 1 Wherein the polymeric article is a braided absorbable suture fabricated in whole or in part from a polymer or copolymer of glycolic acid, glycolide, lactic acid, lactide, dioxanone, trimethylene carbonate, caprolactone, polyalkylene glycol, or combination thereof.

6. The method of claim 1 wherein the storage stabilizing agent comprises a mixture of glycerol and calcium lactate.

7. The method of claim 6 wherein the weight ratio of the components of said mixture is from about 1:1 to 1:10, calcium lactate to glycerol.

8. The method of claim 1 wherein application of the storage stabilizing agent is carried out by coating, spraying or wiping the polymeric article with the agent.

9. The method of claim 1 wherein the polymeric article possesses a moisture content of greater than about 0.5 weight percent.

10. The method of claim 1 wherein the polymeric article possesses a moisture content of up to about 1.5 weight percent at the time it is sealed within a substantially moisture impermeable enclosure therefor.

11. The method of claim 1 wherein the polymeric article retains from about 2 to about 25 weight percent of storage stabilizing agent at the time it is sealed within a substantially moisture impermeable enclosure therefor.

12. A polymeric article which is susceptible to hydrolysis possessing a storage stabilizing amount of stabilizing agent which comprises of a mixture of effective amounts of at least one water soluble hygroscopic polyhydroxy compound or ester thereof and a compound having the general formula

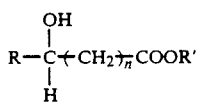

wherein R is hydrogen or methyl, R' is alkali metal or alkaline earth metal and n is 0 or 1 and hydrates thereof.

13. The polymeric article of claim 12 fabricated in whole or in part from a polymer or copolymer possessing short-chain polyester linkages or other readily hydrolyzable linkages.

14. The polymeric article of claim 12 fabricated in whole or in part from a polymer or copolymer of glycolic acid, glycolide, lactic acid, lactide, dioxanone, trimethylene carbonate, caprolactone, polyalkylene glycol, or combination thereof.

15. The polymeric article of claim 12 which is an absorbable suture fabricated in whole or in part from a polymer or copolymer of glycolic acid, glycolide, lactic acid, lactide, dioxanone, trimethylene carbonate, caprolactone, polyalkylene glycol, or combination thereof.

16. The polymeric article of claim 12 wherein the storage stabilizing agent comprises a mixture of glycerol and calcium lactate.

17. The polymeric article of claim 16 wherein the weight ratio of the components of said mixture is from about 1:1 to about. 1:10, calcium lactate to glycerol.

18. The polymeric article of claim 12 possessing a moisture content of greater than about 0.05 weight percent.

19. The polymeric article of claim 12 possessing a moisture content of from about 0.3 to about 1.5 weight percent.

20. A method for improving the storage stability of a polymeric article susceptible to hydrolysis which comprises applying a storage stabilizing amount of a mixture comprising effective amounts of at least one compound selected from the group consisting of glycerol, monoesters of glycerol derived from low molecular weight carboxylic acids, diesters of glycerol derived from low molecular weight carboxylic acids, ethylene glycol, diethylene glycol, triethylene glycol, 1,3-propanediol, trimethylolethane, trimethylolpropane, pentaerythritol, sorbitol and mixtures thereof and at least one compound having the general formula

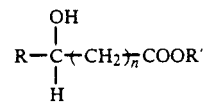

wherein R is hydrogen or methyl, R' is a metal selected from the group consisting of alkali metal and alkaline earth metal and n is 0 to 1 and hydrates thereof, to the polymeric article, as storage stabilizing agent therefor.

21. The method of claim 20 wherein said polymeric article is a surgical article fabricated in whole or in part from a polymer or copolymer of glycolic acid, glycolide, lactic acid, lactide, dioxanone, trimethylene carbonate, caprolactone, polyalkylene glycol or combinations thereof.

22. The method of claim 20 wherein said surgical article is selected from the group consisting of sutures, clips, staples, sponges, gauze, implants and prostheses.

23. The method of claim 20 wherein said storage stabilizing agent further comprises a medico-surgically useful substance.

24. The method of claim 21 wherein the storage stabilizing agent comprises a mixture of glycerol and calcium lactate.

25. The method of claim 23 wherein the medico-surgically useful substance is a tissue growth factor.

26. The method of claim 24 wherein the weight ratio of the components of said mixture is from about 1:1 to 1:10, calcium lactate to glycerol.

27. The method of claim 24 wherein the calcium lactate is calcium lactate pentahydrate.

28. A polymeric article which is susceptible to hydrolysis possessing a storage stabilizing amount of stabilizing agent which comprises a mixture of effective amounts of at least one compound selected from the group consisting of glycerol, monoesters of glycerol derived from low molecular weight carboxylic acids, diesters of glycerol derived from low molecular weight carboxylic acids, ethylene glycol, diethylene glycol, triethylene glycol, 1,3-propanediol, trimethylolethane, trimethylolpropane, pentaerythritol, sorbitol and mixtures thereof and at least one compound having the general formula

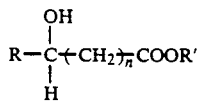

wherein R is hydrogen or methyl, R' is alkali metal or alkaline earth metal and n is 0 or 1 and hydrates thereof.

29. The polymeric article of claim 28 which is a surgical article fabricated in whole or in part from a polymer or copolymer of glycolic acid, glycolide, lactic acid, lactide, dioxanone, trimethylene carbonate, caprolactone, polyalkylene glycol or combination thereof.

30. The polymeric article of claim 28 which is a surgical article selected from the group consisting of a suture, a clip, a staple, gauze, an implant and a prosthesis.

31. The polymeric article of claim 29 wherein the storage stabilizing agent comprises a mixture of glycol and calcium lactate.

32. The polymeric article of claim 28 wherein the storage stabilizing agent further comprises a medico-surgically useful substance.

33. The polymeric article of claim 32 wherein the medico-surgically useful substance is a tissue growth factor.

34. The polymeric article of claim 31 wherein the weight ratio of the components of said mixture is from about 1:1 to 1:10, calcium lactate to glycerol.

35. The polymeric article of claim 31 wherein the calcium lactate is calcium lactate pentahydrate.

36. A storage stabilizing agent for improving the storage stability of a polymeric article susceptible to hydrolysis, said storage stabilizing agent comprising a mixture comprising effective amounts of glycerol and calcium lactate.

37. The storage stabilizing agent of claim 36 wherein the weight ratio of the components of said mixture is from about 1:1 to 1:10, calcium lactate to glycerol.

38. The storage stabilizing agent of claim 36 wherein the calcium lactate is calcium lactate pentahydrate.

39. The storage stabilizing agent of claim 36 further comprising a medico-surgically useful substance.

40. The storage stabilizing agent of claim 39 wherein the medico-surgically useful substance is a tissue growth factor.

41. A method for improving the storage stability of an absorbable surgical suture fabricated from a polymer susceptible to hydrolysis which comprises applying a storage stabilizing amount of a mixture comprising effective amounts of glycerol and calcium lactate to said absorbable surgical suture as storage stabilizing agent therefor.

42. The method of claim 41 wherein the absorbable surgical suture is fabricated in whole or in part from a polymer or copolymer of glycolic acid, glycolide, lactic acid, lactide, dioxanone, trimethylene carbonate, caprolactone, polyalkylene glycol or combinations thereof.

43. The method of claim 41 wherein the calcium lactate is calcium lactate pentahydrate.

44. The method of claim 41 wherein the ratio of the components of said mixture is from about 1:1 to about 1:10, calcium lactate to glycerol.

45. An absorbable surgical suture fabricated from a polymer susceptible to hydrolysis possessing a storage stabilizing amount of stabilizing agent which comprises a mixture of effective amounts of glycerol and calcium lactate.

46. The absorbable surgical suture of claim 45 fabricated in whole or in part from a polymer or copolymer of glycolic acid, glycolide, lactic acid, lactide, dioxanone, trimethylene carbonate, caprolactone, polyalkylene glycol or combinations thereof.

47. The absorbable surgical suture of claim 45 wherein the calcium lactate is calcium lactate pentahydrate.

48. The absorbable surgical suture of claim 45 wherein the ratio of the components of said mixture is from about 1:1 to about 1:10 calcium lactate to glycerol.

* * * * *

UNITED STATES PATENT AND TRADEMARK OFFICE
CERTIFICATE OF CORRECTION

PATENT NO. : 5,051,272
DATED : September 24, 1991
INVENTOR(S) : Hermes et al.

It is certified that error appears in the above-identified patent and that said Letters Patent is hereby corrected as shown below:

Title page:
 Line 8 of the Abstract, "hydreates" should be --hydrates--;

Column 8, line 25, "lactate s" should be --lactate as--

Column 9, line 16, "Wherein" should be --wherein--

Signed and Sealed this

Second Day of March, 1993

Attest:

STEPHEN G. KUNIN

Attesting Officer

Acting Commissioner of Patents and Trademarks